United States Patent [19]

Smith

[11] 4,273,118
[45] Jun. 16, 1981

[54] FIBERS OF HIGH FLUID HOLDING CAPACITY

[75] Inventor: Frederick R. Smith, Toms Brook, Va.

[73] Assignee: Avtex Fibers Inc., Valley Forge, Pa.

[21] Appl. No.: 45,146

[22] Filed: Jun. 4, 1979

[51] Int. Cl.³ ............................................. A61L 15/00
[52] U.S. Cl. ..................................... 128/156; 128/285;
106/164; 106/165; 106/168; 264/188; 264/191;
427/394; 428/288; 428/375; 428/393; 428/913;
536/59
[58] Field of Search ...................... 106/164, 165, 168;
264/186, 188, 191; 427/289, 293, 389.9, 394;
428/288, 375, 378, 393, 913; 128/284, 290 R;
536/59

[56] References Cited

U.S. PATENT DOCUMENTS

| | | | |
|---|---|---|---|
| 3,609,377 | 9/1971 | Pettitt | 536/59 |
| 3,639,665 | 2/1972 | Schweiger | 536/59 |
| 3,702,843 | 11/1972 | Schweiger | 536/45 |
| 3,800,797 | 4/1974 | Tunc | 536/59 |
| 3,804,092 | 4/1974 | Tunc | 536/59 |
| 4,035,569 | 7/1977 | Schweiger | 536/32 |
| 4,063,558 | 12/1977 | Smith | 428/913 |
| 4,064,342 | 12/1977 | Saiko et al. | 536/59 |

Primary Examiner—James J. Bell
Attorney, Agent, or Firm—A. R. Eglington

[57] ABSTRACT

Alloy fibers having high fluid-holding capacity, and a method for making the same, the alloy fibers being comprised of a matrix of regenerated cellulose having 5 to 25 weight percent of alkali metal salts of cellulose sulfate being dispersed therein. The sulfate salts may be present in combination with anionic polymer. The high fluid-holding capacity is at least 4.8 ml per grams as measured by the Demand Absorption Test.

15 Claims, 1 Drawing Figure

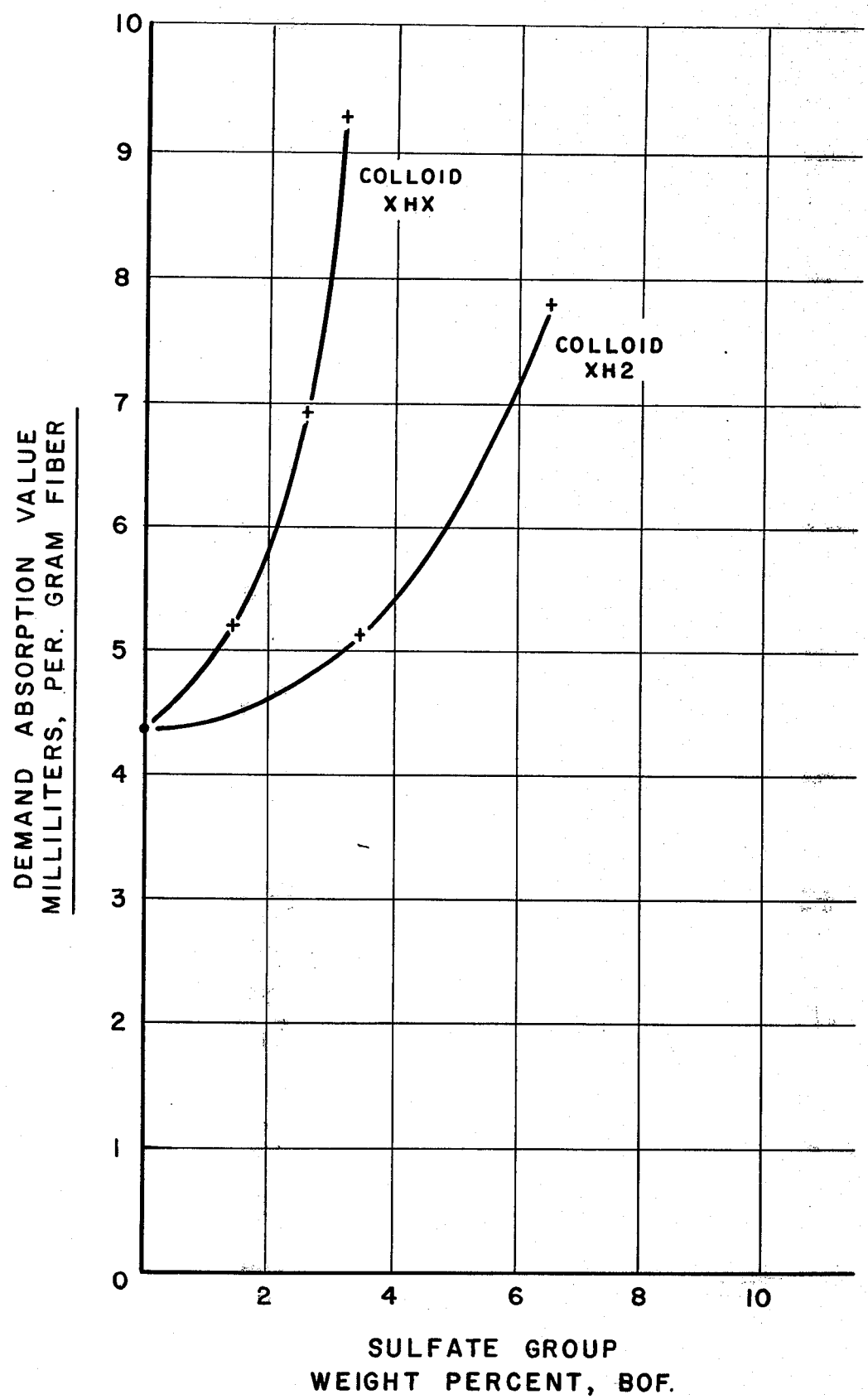

FIBERS OF HIGH FLUID HOLDING CAPACITY

This invention relates to novel alloy rayon staple fibers containing 5 to 25 weight percent of an alkali metal salt of cellulose sulfate and having high fluid holding capacity of at least 4.8 cc per gram, as measured by the Demand Absorption Test.

The art has suggested a number of polymeric or copolymeric materials as additives to viscose rayon, to confer high fluid holding properties on the rayon staple so that it may be adapted to absorption of body fluids and catamenial applications. Examples are: polyacrylic acid salts of alkali metals, U.S. Pat No. 3,844,287; polyvinyl pyrrolidone, U.S. Pat. No. 4,041,121; carboxyalkylated starch, U.S. Pat. No. 3,847,636; and alkali salts of alginic acid, U.S. Pat. No. 4,063,558.

While technical feasibility has been seen with prior art additives, manufacturing complication with high fluid holding (HFH) alloy rayons have fostered a continuing search for new viscose additives that could exhibit consistently high fluid absorption, and compatibility with the viscose rayon manufacturing facilities, while involving only modest cost increases.

The alloy fibers of the present invention meet these criteria and have shown important further processing advantages, as compared to earlier HFH alloy rayons, among which are: (a) minimal tendency of the novel cellulose sulfate additive to form troublesome agglomerates when in the spin bath system; (b) more effective bleaching of staple with hypochlorite treatment; (c) reduced tendency to staple discoloration in the drying step; and (d) better adaptability to the wet manufacturing purification process employed in regular rayon.

The fiber has lower pH's, in both water and saline solutions than those which characterize some other types of HFH alloy rayon; e.g., an alloy rayon based on sodium polyacrylate where such fibers are used for catamenial devices; this brings the fiber closer to the pH range of the body fluids they will be absorbing; thus minimizing pH imbalances with body mucosa.

According to the present invention, there is provided a mixed polymer fiber comprising cellulose sulfate salts and regenerated cellulose, which is prepared by mixing a solution of cellulose sulfate salt with viscose, spinning the resulting solution in a viscose rayon spinning system, processing the fiber by washing successively with water, sodium hydroxide or sodium sulfide solution, water, sodium hypochlorite solution (optional), water, a finish solution and finally drying. Masses of the fiber so prepared have fluid holding capacity significantly higher than ordinary rayon fiber and have a pH in water near 7.

BRIEF DESCRIPTION OF THE DRAWING

In the single FIGURE comprising the drawing is a plot showing the performance of exemplary Colloids of this invention. Demand Absorption values for two such Colloids have been plotted against a calculated value for the percent of sulfate group contained in those Colloids, based on cellulose.

A typical cellulose sulfate, alkali metal salts, of this invention were obtain from Stauffer Chemical Co., Stamford, Conn. They are offered as the Colloid XH series, which are cellulose sulfates with a variable degree of substitution (D.S.); this is an expression of the average number of sulfate groups per anhydroglucose unit of the cellulose. The materials are supplied as granular, cream-colored solids.

Candidate Colloid XHX has a degree of substitution (D.S.) of about 0.3 to 0.4; Colloid XHO has a D.S. range of about 0.4 to 0.7; and Colloid XH2 has a D.S. of about 1.0 to 1.3.

Supplier literature identifies also Colloid XH1 and XH3 differing from the above in degree of substitution. Colloid XH1 has D.S. of 0.7 to 1.0 and Colloid XH3 has D.S. of 1.3 to 1.6.

Typical chemical syntheses are well reported in the literature and forms no part of this invention - Cf. Schweiger, Carbohydrate Res. 1972, 21 (2), 219–28; Pettitt et al U.S. Pat. No. 3,609,377, Stabilized Alkali Metal Salts of Cellulose Sulfate (1971); Schweiger U.S. Pat. No. 3,624,069 (1971) "Process of Preparing a Gellable Colloidal Cellulose Sulfate and Product"; Schweiger U.S. Pat. No. 3,702,843 (1972); Schweiger U.S. Pat. No. 4,035,569 (1977) "Preparation of Cellulose Nitrite"; and U.S. Pat. No. 3,639,665, Schweiger (1972) "Process of Preparing a Gellable Colloidal Cellulose Sulfate";

U.S. Pat. No. 1,848,524, Hagedorn et al;
U.S. Pat. No. 2,539,451, Malm et al;
U.S. Pat. No. 2,559,914, Frank (1951); and
U.S. Pat. No. 3,753,337, Klug (1956)

Cellulose sulfate materials may be prepared by a two-step process in which there is first prepared cellulose nitrite by reaction of cellulose with $N_2O_4$ in dimethylformamide (DMF). A solution results which is reacted with DMF-$SO_3$ complex to give a mixed cellulose nitrite-sulfate ester. The mixed ester is hydrolyzed with water which removes the nitrite groups. The residual cellulose sulfate is neutralized using (e.g.) sodium carbonate yielding sodium cellulose sulfate. Additional description of the preparation may be found in:

(1) "New Cellulose Sulfate Derivatives" by R. G. Schweiger, a paper presented in part at the 175th ACS meeting in Anaheim, California.

(2) "Carbohydrate Sulfates" edited by R. G. Schweiger (ACS Symposium Series 77) page 161 through 172, especially pp. 169 and 171.

An exemplary cellulose sulfate preparation per U.S. Pat. No. 4,035,569 follows.

Cotton linter pulp (400 g.) having a moisture content of about 5–6% was mixed with 2 l. of DMF in a double planetary mixer with cooling and under exclusion of moisture, and 600 g. of $N_2O_4$ was added over a period of about 30 minutes to result in a cellulose trinitrite ester. Then, a DMF-$SO_3$ slurry in DMF containing about 200 g. of $SO_3$ was added slowly over a period of about 30 minutes and mixing continued for another 10–15 minutes. An amount of 485 g. of isobutyl alcohol was added slowly, and the mixture was neutralized (pH 7–8) by the addition of an aqueous solution of sodium carbonate or a slurry of sodium carbonate in a saturated solution or by the addition of dry sodium carbonate. Good and thorough mixing was required for this neutralization step, and generally the presence of water produced better results. The temperature of the reaction mixture was maintained below about 200° C. throughout the reaction until neutralization was complete, and up to the neutralization step, the reaction was carried out under exclusion of moisture. The neutral mixture was then pressed out or centrifuged, and if the solids were too soft to be pressed out, some isopropanol was added to harden them sufficiently. The solids were suspended in about 60–70% aqueous isopropanol, pressed out again, dried and milled. For higher purity, the solids were suspended in aqueous isopropanol a second and, if necessary, a third time before final drying and milling.

The filtrates were combined and subjected to fractional distillation for solvent recovery. One of the fractions distilled at about 66°–67° C. and was identified as isobutyl nitrate, the yield being over 80%. The brown, crystalline residue from distillation contained the theoretical amount of sodium nitrite. An aliquot of it was purified by recrystallization.

In other identical experiments, the isobutyl alcohol was replaced by n-propanol, amyl alcohol, and ethylene glycol. Instead of isobutyl nitrite, the corresponding nitrite esters of n-propanol, amyl alcohol, or ethylene glycol were recovered, but otherwise results were similar. In another similar experiment where the isobutanol was replaced by an equivalent amount of water similar results were obtained, but the residue from the solvent recovery contained equivalent amounts of sodium nitrite and sodium nitrate in theoretical yields. Part of the residue was recrystallized to result in a purified salt mixture.

The sodium cellulose sulfate had a D.S. of 1.0–1.1, and a 1% aqueous solution had a viscosity of 1500–200 cps.

In another experimental series, products were obtained under similar conditions, but the amount of $SO_3$ used for the sulfation was reduced to obtain products with D.S. values of about 0.4, 0.6, and 0.9. These D.S. values were attained with the theoretically calculated amounts of $SO_3$, and 1% aqueous solutions of the products had viscosities ranging between about 5000 and 2000 cps. In another experiment, the amount of $N_2O_4$ was reduced to about 300 g. and that of $SO_3$ increased to about 300 g. to result in sodium cellulose sulfate esters with a D.S. of 1.5–1.6 having 1% aqueous viscosities of about 600–700 cps.

Other cellulose materials, such as wood cellulose or cellulose from vegetable hulls were used with equal success, but the final products had a somewhat lower solution viscosity than those from high D.P. cotton linter pulp. Also neutralization could be carried out equally well with carbonates, bicarbonates and hydroxides of the other alkali metals, such as lithium and potassium, of alkali earth metals, such as magnesium and calcium, and of manganese, cobalt, and nickel and with ammonium hydroxide and amines. In the case of the alkali metals, carbonates and bicarbonates are preferred to the hydroxides because of the high alkalinity of the hydroxides and the danger of degradation.

Samples of fiber have been spun comprising cellulose sulfate (sodium salt) and cellulose. Solutions of cellulose sulfate salt in dilute sodium hydroxide were mixed with viscose and spun into fiber. This fiber was washed with water, caustic soda solution, hypochlorite solution, water and finish solution. The fibers were dried and then evaluated for their fluid holding capacity and pH. The data obtained are presented in Table 1.

Higher fluid holding capacity was achieved with the alloy fibers of this invention than was obtained with alloy rayon incorporating polyacrylic acid salts of alkali metals. (27% greater for Sample 6 (a sample containing Colloid XHX) as compared with Sample 7 (a sample of PA rayon), and 112% greater for Sample 6 as compared with Sample 1 (a control sample containing no additive. Also, as shown in that table the pH of the fiber in the salt form of these samples is just below 7 in water, and is about 6 in 1% saline solution.

Preparation of Additive Solutions

Additive cellulose sulfate solutions were prepared as follows:

Cellulose Sulfate Solution A. To 300 grams of 1% NaOH were added 5 drops of 30% $H_2O_2$, and while stirring, 15 grams of Colloid XHX were added to give a 5% concentration.

Cellulose Sulfate Solution B. To 100 grams of 1% NaOH while stirring, there was added a suspension of 10 grams of Colloid XH2 in 150 grams of methanol to give a 4.0% concentration.

Cellulose Sulfate Solution C. To 500 ml. of 1% NaOH were added, while stirring, 15 grams of Collid XHX giving a 2.91% concentration.

Cellulose Sulfate Solution D. To 650 ml. of 1% NaOH solution was added, while stirring, a suspension of 25 grams of Colloid XHX in 250 grams of methanol to give a 2.7% concentration.

Cellulose Sulfate Solution E. To a 1% NaOH solution was added sufficient Colloid XHO to make a 2% solution.

Viscoses were prepared as follows:

Viscose I. A bright viscose containing 9.5% cellulose, 6.2% NaOH, 29.0% $CS_2$ (b.o.c.) with salt test between 5 and 7 and ball fall visosity of between 40 and 60 seconds.

Viscose II. A dull viscose containing 9.5% cellulose, 6.2% NaOH, 29.0% $CS_2$ (b.o.c.) and 0.5% $TiO_2$ (b.o.c.).

Viscose III. A bright viscose containing 9.5% cellulose, 6.2% NaOH, 31.0% $CS_2$ (b.o.c.) with salt test between 6.5 and 8 and ball fall viscosity between 60 and 80 seconds.

Several samples were spun. As shown below, the proportions of viscose and cellulose sulfate solutions described above were varied. Weighed portions were thoroughly mixed, deaerated under vacuum and then spun.

The spin bath contained about 7% $H_2SO_4$, 1% $ZnSO_4$ and 21% $Na_2SO_4$, and was kept at room temperature. When spun, samples were collected on a cylinder using a Leesona style E23753 winder. The fiber is cut on the cylinder and the sections removed and dropped into nearly boiling water. In this and subsequent steps, the aqueous solution to fiber ratio was about 30 ml. per gram. The processing continued as follows:

1. Ten minutes in distilled water near boiling.
2. Fifteen minutes in distilled water about 25° C.
3. Ten minutes in 0.5% NaOH.*
4. Two or three washes in distilled water.*
5. Three minutes in 0.25% sodium hypochlorite solution.*
6. Two or three washes of several minutes each in distilled water.*
7. Fifteen minutes in 0.2% ACHO 7596T** finish solution.*
8. Centrifuge and dry at 70° C.

*Steps 2 thru 7 are conducted between 20° and 30° C.
**A polyoxyethylene sorbitan monoester of lauric acid.

EXAMPLE I

Fiber Sample 1, Control, Using Viscose I, the resulting fiber had demand absorption values of 4.40, 4.04 and 4.30 cc/g. The average was 4.25 cc/g.

EXAMPLE II

Fiber Sample 2, 10% Colloid XH2 (b.o.c.). Using 300 grams of Viscose I with 71.25 grams of cellulose sulfate solution B, the fiber had demand absorption values of 5.15, 5.10 and 5.10 cc/g. The average was 5.12 cc/g.

EXAMPLE III

Fiber Sample 3, 20% Colloid XH2 (b.o.c.). Using 300 grams of Viscose I with cellulose sulfate solution B, the fiber had demand absorption values of 7.65, 8.15 and 7.60 cc/g. The average was 7.8 cc/g. These fibers had pH measurements in water of 6.90 and 6.87; and in 1% saline solution pH values were 6.10 and 6.08.

AHCO is trademark of ICI Americas.

EXAMPLE IV

Fiber Sample 4, 9.38% Colloid XHX (b.o.c.). Using 300 grams of Viscose I with 53.44 grams of cellulose sulfate solution A, the fiber had demand absorption values of 5.25. 5.15, and 5.10 cc/g. The average was 5.17 cc/g.

EXAMPLE V

Fiber Sample 5, 18.8% Colloid XHX (b.o.c.). Using 300 grams of Viscose I with 107 grams of cellulose sulfate solution A, the fiber had demand absorption values of 7.00, 7.10 and 6.75 cc/g. The average was 6.95 cc/g. These fibers had a pH of 6.9 in water and a pH of 6.08 in 1% saline solution.

EXAMPLE VI

Fiber Sample 6, 24% Colloid XHX (b.o.c.). Using 500 grams of Viscose Solution B with 391.3 grams of cellulose sulfate solution C, the fiber had demand absorption values of 9.4, 9.1 and 9.3 cc/g. The average was 9.27 cc/g. This fiber had a pH in water of 6.48.

EXAMPLE VII

Fiber Sample 7, 20% sodium polyacrylate (b.o.c.) was spun and processed as described above using a sample of viscose from a rayon production machine used to spin PA alloy rayon. The demand absorption values were 7.3, 7.2 and 7.2 cc/g. The average was 7.23 cc/g and the fiber had a pH of 9.0 in water.

EXAMPLE VIII

Fiber Sample 8 was a portion of commercially available PA alloy rayon. It had demand absorption values of 6.75, 6.65 and 6.70 cc/g. The average was 6.70 cc/g.

EXAMPLE IX

Fiber Sample 9, 28.1% Colloid XHX (b.o.c.). Using 300 grams of Viscose I with 160.4 grams of cellulose sulfate solution A, the fiber was difficult to card and the fiber did not wet out uniformly during the fluid holding test.

EXAMPLE X

Fiber Sample 10, 30% Colloid XH2 (b.o.c.). Using 300 grams of Viscose I with 213.75 grams of cellulose sulfate solution B, the fiber was difficult to card and the fibers did not wet out uniformly.

The Demand Absorption values of the foregoing have been plotted against a calculated value for percent sulfate group based on cellulose. For each of the cellulose sulfates the mid-range of substitution was assumed. That plot is shown in the FIGURE.

EXAMPLE XI

Experiments to determine the effect of Colloid XHX and Colloid XH2 addition to a spin bath were made. This is necessary consideration because experience with PA rayon has shown that polyacrylic acid lost to the spin bath reacts with spin bath components to give a second phase material which with age becomes a very tough elastic deposit. A synthetic spin bath, containing 50 ppm of a commerically available cationic nitrogenous spin bath additive, was stirred while adding solutions of the above cellulose sulfates sufficient to give 50 ppm in the spin bath. Colloid XHX was not spin bath soluble but Colloid XH2 dissolved. In both cases the gel which separated did not form any similar second phase elastic deposit.

Similar experiments were made without said additive in the spin bath. The results were the same.

Numerical results for evaluations conducted on the foregoing fiber samples, as to both water held and fiber pH, are set forth in Table I.

EXAMPLE XII

Fiber Sample 11, 10% Colloid XHO (b.o.c.). using 500 grams of Viscose III with 237.5 grams of cellulose sulfate solution E, the fiber had demand absorption values of 6.80 and 6.95 and fluid holding capacity as measured by the Syngyna* test of 5.6 cc/g.

*The Syngyna Method was described by G. W. Rapp in a June 1958 publication of the Department of Research, Loyola University, Chicago, Ill.

EXAMPLE XIII

Fiber sample 12, 20% Colloid XHO (b.o.c.). Using 400 grams of Viscose III with 380 grams of cellulose sulfate solution E, the fiber had fluid holding capacity as measured by the Syngyna test of 9.9. cc/g.

Crimp is a desirable feature in some applications. A suitable crimp level is at least about 8 distinct crimps per inch (such as about 8 to 20). Discussions of chemical crimping of non-alloy rayon fibers are found, for instance, in Merion et al. U.S. Pat. No. 2,517,694; Textile Research Journal, Vol. 23 pp. 137-157 and *Man-Made Fibres* by Moncrief (6th Edition, 1974, publ. by John Wiley & Sons pp. 191-193).

While for most uses the fibers need not have high strength properties, the alloy fibers have been found to retain to a very large extent the physical properties of non-alloy rayon. Typically, the alloy fibers of this invention are not brittle and may be processed in about the same ways as ordinary rayon.

While the polyoxyethylene sorbitan monoester of a higher fatty acid (such as AHCO* 7596T) is a preferred finish, it is within the broader scope of the invention to employ other lubricating or protective finishes, preferably applied in aqueous solution or dispersion, such as soaps, sulfonated oils; ethoxylated fatty acids; ethoxylated fatty ester of polyhydric alcohols; fatty acids esters combined with emulsifying agents or mixtures of various lubricating finishes. Generally, the amount of lubricating finish deposited on the fiber will be well below 1%, and usually more than 0.05%, such as in the range of about 0.1 to 0.5% or 0.1 to 0.3%. Preferably it is not such as to give the fibers an oily feel.

*A trademark

The degree and type of fiber lubrication and the degree of conversion to salt form are such that the wet lubricated fibers have considerable resistance to compaction and tend to separate from each other after they have been squeezed together (to express excess water) under pressure and then released. Thus when the fibers are dried they show little tendency to adhere to neighboring fibers, and the product (particularly after rayon "opening" on typical textile equipment used for that purpose) is made up substantially entirely of individual nonbonded fibers.

The alloy fibers of the present invention are adapted for use in a variety of articles, such as surgical dressings, pads and vaginal tampons, in which high fluid retention is an essential characteristic. In the manufacture of such articles, the alloy fibers of this invention may be used in the same manner and with the same equipment as employed with rayon fibers and they may be blended with other fibers which may or may not enhance the absorbent properties of the resulting articles. Fibers with which the alloy fibers of the present invention may be blended include, for example, rayon, cotton, chemically modified rayon or cotton, cellulose acetate, nylon, polyester, acrylic, polyolefin, etc. Typically a tampon is an elongated cyclindrical mass of compressed fibers, which may be supplied within a tube which serves as an applicator; see U.S. Pat. Nos. 2,024,218; 2,587,717; 3,005,456; 3,051,177. The fiber of this invention has been converted into yarns and woven into fabrics having textile applications.

The cellulose sulfate salt may be the sole high polymeric additive in the viscose or it may be used together with other water-soluble high polymers, including those which are aqueous alkali-soluble. Preferably, these are anionic polymers such as polymeric acids or salts thereof (e.g., alkali metal salts), salts of carboxyalkyl celluloses (such as sodium carboxyethyl cellulose), salts of polyacrylic acids (including polyacrylic acid or polymethacrylic acid, or their copolymers, with one or more other monomers such as acrylamide or alkyl acrylates, e.g., ethyl acrylate), salts of polymers or copolymers of maleic or itaconic acid with other monomers such as methyl vinyl ether, or naturally occurring polycarboxylic polymers, such as algin.

These materials are preferably dissolved in an aqueous medium before addition to the viscose, the solution being preferably alkaline, e.g., they may be made with an amount of alkali (caustic soda), stoichiometrically equivalent to the amount of acidic (e.g., sulfate) groups of the polymer or with an excess of alkali. Less desirably, these materials may be added in acid form (again, preferably as aqueous solutions) and be converted to salt form by the action of the alkali present in the viscose.

When another anionic polymer is present, it is within the broader scope of the invention to reduce the proportion of the cellulose sulfate; for instance, one may use, say, 7% sodium polyacrylate and 8% sodium salt of cellulose sulfate (b.o.c.) or 10% of each of these. Other water-soluble high polymers include polyvinyl pyrrolidone, or substantially non-ionic polymers such as starch (which may be added as, say, an alkaline solution containing some 2–5% of NaOH) or polyvinyl alcohol.

Polymers which may be used with, or in place of, cellulose sulfate salts include carbohydrate sulfate salt, e.g., starch sulfate salt, polyol sulfate salts, such as would be derived from treatment of polyvinyl alcohol, hydroxyethyl cellulose, partially methylated cellulose, agar, guar gum, dextrins, or other polymers having accessible hydroxyl groups; and carrageenan, fucoidan, furcellaram, or other natural sulfate containing polymers.

Terpolymer combination with the cellulose sulfate salt-cellulose system could include polyvinyl pyrrolidone, polyacrylamide, polyvinyl alcohol, polyethylene oxide, polyacrylic acid, polymethacrylic acid, or copolymers of combinations for the antecedent monomers of these polymers. The third polymer could also be chosen from natural materials, such as starch, guar gum, sodium alginate, or from carboxylated or phosphorylatedderivates.

DEMAND ABSORPTION TEST

This test is an adaptation of procedures described by by Bernard M. Lichstein in "Demand Wettability, A New Method for Measuring Absorbency Characteristics of Fabrics", a paper read at the INDA Conference, March 1974. A schematic drawing of the apparatus is depicted in the paper, wherein the plunger is free to move vertically or rotate in the guide.

Procedure for calculating water held in cc. per gram of Fiber (a) Weigh 2.00 grams of carded rayon.
(b) Place the fiber in a 1 inch diameter die.
(c) Place the die with fiber in a press and compress the fiber array to a thickness of 0.150 inches and hold 15 seconds.
(d) Remove the pellet from the die and place it on the sample support. (Note: The sample support and the foot of the plunger are each 1 inch in diameter. The pellet of fiber should not extend beyond the edge of the support or plunger.
(e) Record the liquid level in the burette.
(f) Open Valve A and then Valve B. (See schematic of above article)
(g) If flow does not start spontaneously, then cause flow to start by placing a finger over the open tee and squeeze the bulb. Remove the finger from the tee.
(h) Allow flow to continue until no more bubbles enter the burette (or bubbles are 90 seconds apart).
(i) Record the liquid level in the burette. Close Valve B and then Valve A.
(j) Remove the pellet and prepare the apparatus for the next test.
(k) Report demand absorption by subtracting the first burette reading (e) from the second (c) and divide by 2. The dimensions of the result are cc. per gram.

CALCULATION OF PLOT OF DEMAND ABSORPTION VALUE VS. SULFATE GROUP

The calculation of points used in plotting the curves of the FIGURE was done as folows:

$$\% \ SO_4 \ bof = \left( \frac{\% \ \text{cellulose sulfate boc} \times \frac{(SO_4) \times DS}{162 + 102 \times DS}}{100 + \% \ \text{cellulose sulfate boc}} \right) 100$$

wherein

% $SO_4$ bof is percent sulfate based on dry fiber.

% cellulose sulfate boc is the added percent cellulose sulfate based on the non-sulfated cellulose in the viscose.

$SO_4 = 96$ (The formula weight.)

DS is the degree of substitution for the cellulose sulfate used. 162 is the formula weight of the anhydrogulucose unit of which cellulose is the polymer.

102 represents the formula weight of sodium sulfate group and is derived as follows. The addition to cellulose of sodium sulfate group may be written: (with formula weights)

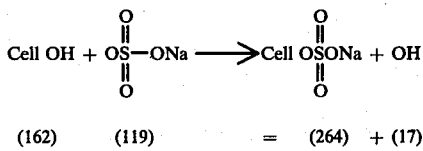

(162)  (119)     =   (264) + (17)

Then cellulose sulfate, at any DS, is

162+(119−17) X DS or 162+102 X DS

100+% cellulose sulfate (boc) represents the weight of dry fiber containing 100 parts of non-sulfated cellulose plus the added percentage of the cellulose sulfate.

The data plotted is set forth in Table II.

TABLE I

| # Fiber Sample | Water Held,* cc/g | Water pH | Saline pH |
|---|---|---|---|
| 1. Control (No additive) | 4.37 | — | — |
| 2. 10% Colloid XH2 (boc) | 5.12 | — | — |
| 3. 20% Colloid XH2 (boc) | 7.8 | 6.89 | 6.09 |
| 4. 9.38% Colloid XHX (boc) | 5.17 | — | — |
| 5. 18.8% Colloid XHX (boc) | 6.95 | 6.90 | 6.08 |
| 6. 24.0% Colloid XHX (boc) | 9.27 | 6.48 | — |
| 7. PA Rayon Control** | 7.32 | 9.0 | — |
| 8. PA Alloy Rayon Avtex Fiber** | 6.70 | — | — |
| 9. 28.1% Colloid XHX (boc) | — | — | — |
| 10. 30.0% Colloid XHX (boc) | — | — | — |

*Demand Absorption Test described earlier.
**Spinning solution contained 20% sodium polyacrylate (boc).

TABLE II

DEMAND ABSORPTION VALUE VS. WEIGHT PERCENT SULFATE GROUP

| % Cellulose Sulfate boc | Colloid XHX | | Colloid XH2 | |
|---|---|---|---|---|
| | % SO4 in Fiber | Demand Absorption | % SO4 in Fiber | Demand Absorption |
| 9.38 | 1.46 | 5.17 | — | — |
| 10.00 | — | — | 3.59 | 5.12 |
| 18.77 | 2.69 | 6.95 | — | — |
| 20.00 | — | — | 6.59 | 7.80 |
| 24.00 | 3.29 | 9.27 | — | — |

What is claimed is:

1. An article of manufacture comprising a highly fluid absorbent mass of alloy fibers, said fibers comprising a matrix of regenerated cellulose and a cellulose sulfate salt of an alkali-metal dispersed therein, said salt being present in an amount of at least about five weight percent based on the weight of the cellulose.

2. The article of claim 1 wherein said cellulose sulfate salt is present in the regenerated cellulose in an amount ranging from about 5 to about 25 weight percent based on the weight of the cellulose.

3. The article of claim 1 wherein the fibers have a lubricating and protective finish thereon.

4. The article of claim 1 in the form of a surgical dressing.

5. The article of claim 1 in the form of a tampon.

6. An article as in claim 3 wherein said lubricating or protective finish comprises a partial higher fatty acid ester of sorbitan or mannitan or of a polyoxyethylene derivative thereof.

7. An article as in claim 3 wherein said fibers are staple fibers, said article comprising a non-woven array of said staple fibers.

8. An alloy fiber comprising a matrix of regenerated cellulose and a cellulose sulfate salt of an alkali-metal dispersed therein, said salt being such, and present in such proportion, within the range of about 5 to 25 percent, based on the weight of cellulose, and that the "fluid-holding capacity" (as hereinabove defined) is at least 4.8 cc/g as measured by the Demand Absorption Test.

9. Fiber as in claim 8, said fiber being in staple form, said alkali metal being sodium and said salt being present in an amount of at least 10 percent based on the weight of cellulose.

10. Alloy rayon staple fibers as in claim 8 produced by incorporating sodium salt of cellulose sulfate, in said proportion, into viscose solution, spinning the mixture into an acidic spin bath containing sulfuric acid and sodium sulfate to regenerate the fiber to form a stretchable fiber, stretching said fiber in a hot aqueous medium, cutting said stretched fibers into staple form, relaxing said cut fibers in a hot water bath, washing said cut fibers and applying said alkaline treatment in aqueous medium, the acidity of said stretched fibers being neutralized to such an extent during said process that at least about three-fourths of said sulfate groups are in sodium salt form.

11. A fiber as in claim 8 having a lubricating or protective finish thereon.

12. A method of preparing highly fluid absorbent alloy rayon fibers comprising mixing a cellulose sulfate salt of alkali-metal with a filament-forming viscose whereby the viscose predominates in the mixture, forming the mixture into fibers, coagulating and regenerating the fibers, applying a lubricating and protective finish to said fibers, and drying the fibers in the form of an alkali-metal salt, the proportion of said sulfate salt added to said viscose being at lest about 5% based on cellulose.

13. A method as in claim 12 wherein said alkali-metal salt in said fibers is present in such proportion, that the "fluid-holding capacity" (as hereinabove defined) is at least 4.8 cc/g.

14. A method as in claim 12 wherein said salt is a sodium salt.

15. A method as in claim 12 and including the step of cutting the fibers into staple form before drying.

* * * * *

UNITED STATES PATENT AND TRADEMARK OFFICE
CERTIFICATE OF CORRECTION

PATENT NO. : 4,273,118
DATED : June 16, 1981
INVENTOR(S) : Frederick R. Smith

It is certified that error appears in the above-identified patent and that said Letters Patent are hereby corrected as shown below:

In column 1, line 64, "obtain" should read -- obtained --.
In column 2, line 8, "XH3" should read -- XH3 --.
In column 3, line 24, "200" should read -- 2000 --.
In column 3, line 62, after "XHX)", insert -- ) --.
In column 3, line 65, after "additive", insert -- ) --.
In column 4, line 14, "Collid" should read -- Colloid --.
In column 4, line 55, "ACHO" should read -- AHCO --.
In column 5, line 17, "5.25." should read -- 5.25, --.
In column 6, line 1, after "is" insert the word -- a --.
In column 6, line 20, capitalize "using".
In column 6, line 32, "9.9." should read -- 9.9 --.
In column 8, line 5, should read -- phosphorylated derivatives --.
In column 8, line 27, after "plunger." insert -- ) --.
In column 8, line 64, should read -- droglucose --.
In column 10, line 48, "lest" should read -- least --.

Signed and Sealed this

Twenty-second Day of September 1981

[SEAL]

Attest:

GERALD J. MOSSINGHOFF

Attesting Officer

Commissioner of Patents and Trademarks